United States Patent [19]

Shoesmith, deceased

[11] Patent Number: Plant 5,946

[45] Date of Patent: Apr. 14, 1987

[54] CHRYSANTHEMUM PLANT NAMED KEYSTONE

[75] Inventor: Leonard H. Shoesmith, deceased, late of Westfield, England, by May Victoria Shoesmith, executrix

[73] Assignee: Ball Pan Am Plant Company, Parrish, Fla.

[21] Appl. No.: 746,890

[22] Filed: Jun. 20, 1985

[51] Int. Cl.[4] ..... A01H 5/00

[52] U.S. Cl. ..... Plt./78

[58] Field of Search ..... Plt./78

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Keystone having large incurved capitulum form and formal capitulum type; medium yellow ray floret color; diameter across face of capitulum of 11 cm to 14 cm; vigorous growth habit on strong stems; and, uniform 9 week flowering response.

1 Drawing Figure

The present invention comprises a new and distinct cultivar of *Chrysanthemum morifolium,* Ramat., hereinafter referred to by the cultivar name Keystone.

Keystone is a product of a planned breeding program which had the objective of creating new standard Chrysanthemum cultivars having flowers with long incurved ray florets, with the flower being supported on strong stems for year around production. Such traits in combination were not present or needed improvement in previously available commercial cultivars.

Keystone was originated from a hybridization made in a controlled breeding program by Leonard H. Shoesmith in Westfield, Woking, Great Britain in 1978. The male and female parents are unknown at this time.

Keystone was discovered and selected as one flowering plant within the progeny of the stated parentage by or under the supervision of Leonard H. Shoesmith in November of 1979 in a controlled environment in West Chicago, Ill., and given the code #S9-1736-Y.

The first act of asexual reproduction of Keystone was accomplished when vegetative cuttings were taken from the initial selection in February of 1980 in a controlled environment in West Chicago, Ill. by a technician working under formulations established and supervised by Leonard H. Shoesmith. Horticultural examination of selected units initiated February of 1980 has demonstrated that the combination of characteristics as herein disclosed for Keystone are firmly fixed and are retained through successive generations of asexual reproduction.

Keystone has not been observed under all possible environmental conditions. The phenotype may vary significantly with variations in environment such as temperature, light intensity and day length. The following observations, measurements and comparisons describe plants grown in West Chicago, Ill. and Parrish, Fla. under greenhouse conditions which approximate those generally used in commercial practice.

The following traits have been repeatedly observed and are determined to be basic characteristics of Keystone which in combination distinguish this Chrysanthemum as a new and distinct cultivar:

(1) Large incurved capitulum form.

(2) Formal capitulum type.

(3) Medium yellow ray floret color.

(4) Diameter across face of capitulum is 11 cm to 14 cm.

(5) Vigorous growth on strong stems.

(6) Uniform 9 week year around flowering response using photoperiodic control.

(7) Height is 1 to 2 meters, depending on the time of bud initiation and temperature.

Of the many commercial cultivars known to the present inventor, the most similar in comparison to Keystone is Yellow Nobhill. In comparison to Yellow Nobhill, Keystone is one week earlier in response and twice as vigorous. Keystone therefore finishes much taller than Yellow Nobhill. The yellow color and flower type of Keystone are similar to those same characteristics of Yellow Nobhill.

The accompanying photographic drawing shows typical inflorescence of Keystone. The photograph has a black and white background, with the flower representing the true flower color of Keystone. The foliage of Keystone is not unique and therefore does not clearly appear in the photograph.

In the following description, color references are made to The Royal Horticultural Society Colour Chart. The color values were determined in April of 1985 under inflorescent and natural daylight at Bradenton, Fla.

Classification:

*Botanical.*—*Chrysanthemum morifolium,* Ramat., cv Keystone.

*Commercial.*—Standard.

I. INFLORESCENCE

A. Capitulum:

*Form.*—Incurved.

*Type.*—Formal.

*Diameter across face.*—11 cm to 14 cm.

B. Corolla of ray florets:

*Color (general tonality from a distance of three meters).*—Medium yellow.

*Color (upper surface).*—9C.

*Color (under surface).*—9C.

C. Corolla of disc florets:

*Color (mature).*—Insignificant.

*Color (immature).*—Insignificant.

D. Reproductive organs:

*Androecium.*—Present in disc florets only; insignificant.

*Gynoecium.*—Present in both ray and disc florets.

II. PLANT

A. General appearance:

*Height.*—1–2 meters depending on time of bud initiation and temperature.

B. Foliage:

*Color* (*upper surface*).—147A.

*Color* (*under surface*).—147B.

*Shape.*—Deeply lobed and slightly serrated.

It is claimed:

1. A new and distinct cultivar of Chrysanthemum plant named Keystone, as described and illustrated, and particularly characterized by its large incurved capitulum form and formal capitulum type; medium yellow ray floret color; diameter across face of capitulum of 11 cm to 14 cm; vigorous growth habit on strong stems; and, uniform 9 week flowering response.

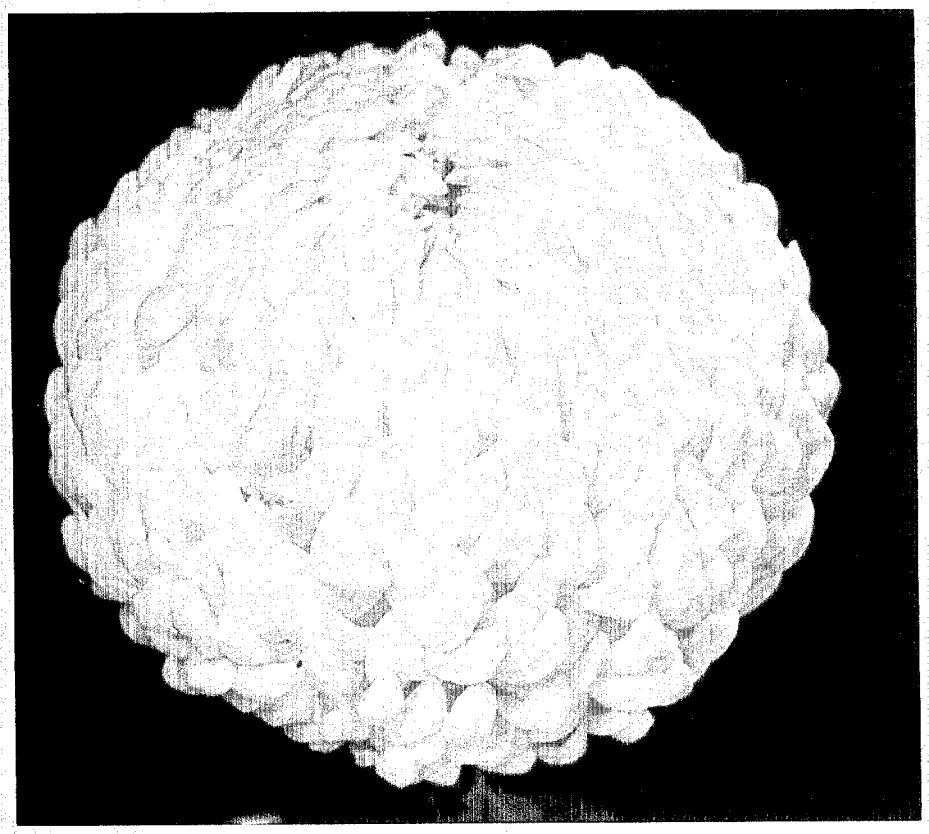

* * * * *